(12) United States Patent
Vilsmeier et al.

(10) Patent No.: US 11,963,723 B2
(45) Date of Patent: Apr. 23, 2024

(54) VISUALIZATION OF MEDICAL DATA DEPENDING ON VIEWING-CHARACTERISTICS

(71) Applicant: Brainlab AG, Munich (DE)

(72) Inventors: Stefan Vilsmeier, Munich (DE); Christoffer Hamilton, Aschheim (DE)

(73) Assignee: Brainlab AG, Munich (DE)

( * ) Notice: Subject to any disclaimer, the term of this patent is extended or adjusted under 35 U.S.C. 154(b) by 719 days.

(21) Appl. No.: 17/046,619

(22) PCT Filed: Jun. 11, 2018

(86) PCT No.: PCT/EP2018/065387
§ 371 (c)(1),
(2) Date: Oct. 9, 2020

(87) PCT Pub. No.: WO2019/238214
PCT Pub. Date: Dec. 19, 2019

(65) Prior Publication Data
US 2021/0113269 A1 Apr. 22, 2021

(51) Int. Cl.
*A61B 34/10* (2016.01)
*G02B 27/01* (2006.01)
*G06F 3/01* (2006.01)

(52) U.S. Cl.
CPC ............ *A61B 34/10* (2016.02); *G02B 27/017* (2013.01); *G06F 3/011* (2013.01); *A61B 2034/102* (2016.02); *A61B 2034/107* (2016.02)

(58) Field of Classification Search
CPC .............. A61B 34/10; A61B 2034/102; A61B 2034/107; G02B 27/017; G06F 3/011; G06F 3/012; G06F 3/013
See application file for complete search history.

(56) References Cited

U.S. PATENT DOCUMENTS

| | | | |
|---|---|---|---|
| 9,740,284 B2 * | 8/2017 | Sullivan | G06V 40/193 |
| 2005/0203380 A1 | 9/2005 | Sauer et al. | |
| 2012/0075343 A1 * | 3/2012 | Chen | G06T 19/006 |
| | | | 345/633 |
| 2013/0128364 A1 | 5/2013 | Wheeler et al. | |
| 2014/0267419 A1 * | 9/2014 | Ballard | G06T 11/00 |
| | | | 345/633 |
| 2016/0077547 A1 | 3/2016 | Aimone et al. | |

(Continued)

FOREIGN PATENT DOCUMENTS

| | | |
|---|---|---|
| EP | 2452649 | 5/2012 |
| WO | 2019110135 | 6/2019 |
| WO | 2019238214 | 12/2019 |

OTHER PUBLICATIONS

Voelker, "Eye Tracking in Surgical Robotics" JAMA. vol. 318, No. 19. Nov. 21, 2017. Retrieved from https://jamanetwork.com/journals/jama/articleabstract/.

(Continued)

*Primary Examiner* — Maurice L. Mcdowell, Jr.
(74) *Attorney, Agent, or Firm* — Gray Ice Higdon

(57) ABSTRACT

The present invention relates to a computer-implemented medical method, a computer program and a medical system (1) for providing, in a medical environment, an AR-overlay that is projected into the field of view provided by an AR-device (4) as a function of the characteristics of a user's (5) view with respect to an observed object (6).

14 Claims, 3 Drawing Sheets

(56) References Cited

U.S. PATENT DOCUMENTS

| | | |
|---|---|---|
| 2016/0086380 A1 | 3/2016 | Vayser et al. |
| 2016/0225192 A1* | 8/2016 | Jones et al. |
| 2016/0246384 A1* | 8/2016 | Mullins .................. G06F 3/017 |
| 2017/0038831 A1* | 2/2017 | Vidal ..................... G09G 3/001 |
| 2017/0172696 A1 | 6/2017 | Saget et al. |
| 2017/0213387 A1 | 7/2017 | Bean et al. |
| 2017/0367771 A1 | 12/2017 | Tako et al. |
| 2022/0168052 A1* | 6/2022 | Ziraknejad ......... G06F 3/04815 |

OTHER PUBLICATIONS

International Search Report and Written Opinion issued in Application No. PCT/EP2018/065387 dated Feb. 11, 2019. 12 Pages.

\* cited by examiner

VISUALIZATION OF MEDICAL DATA DEPENDING ON VIEWING-CHARACTERISTICS

FIELD OF THE INVENTION

The present invention relates to a computer-implemented method for providing an AR-overlay in a medical environment, which is projected into the field of view provided by an AR-device, and to a corresponding computer program, a non-transitory program storage medium storing such a program and a computer for executing the program, as well as a medical system comprising an electronic data storage device and the aforementioned computer.

TECHNICAL BACKGROUND

In recent years, augmented reality (AR) has become more and more popular for a large variety of applications which not only include private applications such as computer games, tour- and sightseeing guides, but of course also educational and commercial applications. Concerning visually augmented reality, a general aim is to provide additional information within a person's "natural" visual perception of the real world. In the field of medical applications, visually augmented reality may be used for providing medical data to surgeons and other medical personnel, such that these persons do not need to look away from the surgical site and towards conventional displays or monitors, but can rather keep their attention on the surgical site while being provided with additional information.

In order to provide such AR-overlays within a person's field of view, a large variety of optical devices are known, including (semi-transparent) displays, eyeglasses/goggles, head-up displays (HUD), contact lenses and so on, most of which have in common that they generate an image in front of or within one or both eyes of the user, thereby supplementing the natural field of view perceived by the eyes of the user.

So far, in case the user wishes to alter the content of or otherwise manipulate the AR-overlay, known systems require a context-switch for the user in order to interact with a device-interface which is remote from the current field of view of the user.

The present invention has the object of enhancing and supplementing augmented reality visualizations in a comfortable and convenient manner for the user.

The present invention can be used for any medical, surgical or therapeutical procedures e.g. in connection with a system for image-guided radiotherapy such as Curve® and ExacTrac®, both products of Brainlab AG.

Aspects of the present invention, examples and exemplary steps and their embodiments are disclosed in the following. Different exemplary features of the invention can be combined in accordance with the invention wherever technically expedient and feasible.

Exemplary Short Description of the Invention

The present invention relates to a computer-implemented medical method, a computer program and a medical system for providing, in a medical environment, an AR-overlay that is projected into the field of view provided by an AR-device as a function of the characteristics of a user's view with respect to an observed object.

In the following, a short description of the specific features of the present invention is given which shall not be understood to limit the invention only to the features or a combination of the features described in this section.

The disclosed method encompasses utilizing an AR-device as it is described above, but wherein the content of the provided AR-overlay is manipulated as a function of one or more characteristics of a user's view with respect to an object observed by the user via the AR-device. As it will be described in more detail in the following chapters, the one or more viewing-characteristics is determined on the basis of the relative spatial position (i.e. the relative spatial location and/or the relative spatial orientation) between the AR-device and the observed object and/or the eyes of the user and the observed object. In more specific words, the AR-overlay provided to the user is manipulated on the basis of the user's head pose and/or viewing direction with respect to the object. Thus, the present invention allows the user of an AR-device to stay focused on an area of concern while manipulating the content of the provided AR-overlay.

General Description of the Invention

In this section, a description of the general features of the present invention is given for example by referring to possible embodiments of the invention.

In general, the invention reaches the aforementioned object by providing, in a first aspect, a computer-implemented medical method of providing an AR-overlay in a medical environment, which is projected into the field of view provided by an AR-device, particularly by AR-goggles, as a function of predefined viewing-characteristics, wherein the method comprises the following steps:
   a) position data is acquired, describing the spatial position of an object observed through the AR-device relative to the spatial position of the AR-device and/or the spatial position of the eyes of a user of the AR-device;
   b) viewing-characteristics data is determined based on the position data, describing at least one characteristic of the user's view at the object:
   c) visualisation data is determined based on the viewing-characteristics data, describing the AR-overlay which is projected into the field of view provided by the AR-device.

The method comprises executing, on at least one processor of at least one computer (for example at least one computer being part of a medical navigation system), the method steps described herein.

In a first basic step of the inventive method, the relative spatial position between the currently observed object and the AR-device and/or the eyes of the user is determined. For this purpose, a medical tracking system (external or contained within the AR-device) can be utilized which may either directly recognize the object, the AR-device and/or the user's eyes, for example by applying shape recognition methodologies on video images acquired by one or more optical cameras, or by recognizing tracking markers assigned to the object and/or the AR-device, such that the spatial position (spatial location and/or spatial orientation) of the object and at least one of the AR-device and the user's eyes is known in three dimensional space. In this respect, the system may recognize whether or not an object is "observed" as a result of a user input. For example, such an object may be selected by aiming the visual axis of the AR-device at the object and either triggering a selection signal, for example by blinking intentionally, or by keeping the visual axis on the object for a predefined amount of time. The object may however also be predefined as the "observed object". For example, for performing surgery on a brain tumor, said tumor may be preselected as "observed object".

From this positional data acquired, the relative spatial position of the object with respect to at least one of the AR-device and the user's eyes can be calculated such that, in a second basic step of the inventive method, one or more characteristics of the user's view at the object, which are described in more detail further below, can be determined.

In a third basic step of the inventive method, the AR-overlay provided to the user via the AR-device is generated based on the at least one determined viewing characteristic.

For example, one viewing-characteristic described by the viewing-characteristics data is the spatial direction of the visual axis of the AR-device or of the visual axis of the user's eyes towards the object. In other words, it is analyzed from which spatial direction the user is looking at the object. For example, the user may look at the object from the left side of the object, and then change his position so as to look at the object from the right side of the object. Dependent on the direction from which the user is looking at the object, the content of the provided AR-overlay may change. Further, the content of the AR-overlay may for example only depend on a horizontal component or a vertical component of the spatial viewing direction, thereby leaving the respective other component unrecognized.

Additionally or alternatively, the viewing-characteristics data may describe at least one of the following characteristics of the user's view with respect to the object:
- a first deviation angle between a visual axis of the AR-device and a line connecting the object and the AR-device;
- a second deviation angle between a visual axis of the eyes and a line connecting the object and the eyes;

particularly wherein the viewing-characteristics data describes a horizontal component and/or a vertical component of the first and/or second deviation angle.

In other words, the viewing-characteristics data may recognize whether the visual axis of either the AR-device or the user's eyes deviates from the direction towards the object such that it can be determined whether the user is "looking past the object", i.e. the user's viewing direction "misses" the object by a certain amount. For example, depending on whether the user looks to an area left, right, above or below the object of interest, the AR-overlay may contain different or additional content as compared to when the user looks straight at the object. In this respect, it should be noted that in case the overlay content depends on the direction of the AR-device, the user's eyes may still stay focused on the object of interest. Rather, the user may manipulate the AR-overlay by only rotating the head by a certain amount while still looking straight at the object.

Additionally or alternatively to the above viewing-characteristics, the viewing-characteristics data may describe
- a tilt angle of the AR-device around the visual axis of the AR-device, particularly with respect to the gravitational direction and/or
- the distance of the AR-device with respect to the object, particularly along the visual axis of the AR-device.

In other words, the user may tilt his head (rotating the head substantially around the visual axis) so as to manipulate the content of the AR-overlay.

Further, the user may also manipulate the content of the AR-overlay by moving towards or away from the object.

In this respect, it is important to note that the invention distinguishes between changing the AR-overlay as such and changing the content of the AR-overlay. For example, an artificial, three-dimensional-image data set, such as a 3D-CT-scan, which is and stays registered with the "real field of view" as seen through the AR-device has to change as soon as the user moves and thereby changes the field of view as seen through the AR-device. However, the content of the AR-overlay would remain the same, namely the 3D-CT-scan.

On the other hand, changing or manipulating the content of the AR-overlay may comprise but is not limited to changing the amount and/or type of information provided by the AR-overlay, such as adding, removing or changing data provided in a written form or by at least one image projected in the user's field of view. For example, certain written or image information may only appear in the AR-overlay as such in case certain criteria for the viewing characteristics is met.

Further, providing the AR-overlay may also consider the magnitude of an acceleration of the AR-device, i.e. the "intensity" the user changes the head pose or viewing direction. For example, a fast rotation of the head may cause a different AR-overlay to be displayed than a slow rotation of the head.

As the present invention is concerned with providing an AR-overlay in a medical environment, the observed object may in particular be
- an anatomical structure, particularly a pathological structure such as a tumor of a patient;
- a medical device, a medical apparatus, a medical instrument or a medical implant; particularly wherein a plurality of objects is observed, wherein the AR-overlay comprises at least one of:
  - anatomical visualizations including images and/or virtual images of anatomical structures of the patient, which are in particular segmented;
- anatomical information;
- surgery parameters;
- surgery instructions;
  - information on a medical/surgical procedure, particularly on a current and/or subsequent step of the procedure;
- measurements on the patient's anatomy and/or medical implants;

particularly wherein the content of the AR-overlay is positionally registered with the field-of-view provided by the AR-device.

More specifically, the content of the AR-overlay may change in the following respects:
- the visualization of lager structures changes to a visualization of smaller structures, specifically in accordance with a decreasing distance between the AR-device and the object, and vice versa;
- different components or parts of the patient's anatomy are displayed, specifically depending on the spatial direction of a visual axis;
- information on the patient's anatomy is displayed, specifically depending on the tilt angle of the AR-device; and/or
- acquired 2D- and/or 3D-images, measurements, planned craniotomies, trajectories or orientations of instruments or implants are displayed, specifically depending on their alignment with respect to the spatial direction of a visual axis;

specifically wherein the content of the AR-overlay is positionally registered with the field-of-view provided by the AR-device.

In order to determine the at least one viewing characteristic, particularly the spatial relative position between the object and the AR-device and/or the object and the user's eyes, the AR-device may comprise one or more of the following sensors:
- at least one video sensor oriented in a forward direction and substantially aiming to the field-of-view provided by the AR-device;
- at least one video sensor oriented in a backward direction and substantially aiming to at least one eye of the user;
- at least one sensor adapted to sense the spatial position of the AR-device;
- at least one sensor adapted to sense an acceleration of the AR-device;
- at least one sensor adapted to sense the distance between the AR-device and an object, particularly along the visual axis of the AR-device.

In a further example, the field-of-view provided by the AR-device can be darkened out dependent on at least one viewing characteristic, for example by a so-called "shutter mechanism", except for a defined region of interest (e.g. an observed anatomical or pathological structure) so as to avoid distraction of the user.

In the following, a plurality of specific embodiments are described, without limiting these embodiments to all of the features described in the respective context. Rather, the features explained therein can be combined with other features described herein in any feasible manner.

In one embodiment of the present invention, different visualizations of anatomical information are provided as overlays on the real patient anatomy. Depending on the orientation and viewing angle of the head-mounted display, the user sees different parts of the segmented anatomy. E.g. if a patient is lying on his back on a surgical table, the surgeon can see a segmented tumor if looking from above the patient, see blood vessels if looking from the side of the patient and see a cerebrum visualization if looking from behind the patient. Thus, the change of head pose changes the visualization.

In a further embodiment, the actual eye viewing direction in relation to the headset determines which anatomical information shall be displayed. E.g. if a surgeon is operating on a patient's head, tilting the head but keeping the eye viewing direction constant, displays an additional anatomical information overlay. Tilting the head in different directions may display different information. The advantage of this solution is that the surgeon can operate in straight viewing direction without overlays and then tilt his head to get presented with additional visual information.

In a further embodiment, the distance between the patient anatomy and the head mounted display is taken into account for the visualization. E.g. vessel information that is extracted from medical imaging scans is displayed with different thresholding. The distance between head mounted display and patient anatomy is translated to a thresholding value. Thus, approaching the patient leads to smaller vessels becoming visible. Increasing the distance between head mounted display and patient anatomy leads to larger vessels only being displayed. Similarly, the intensity of colors could increase or decrease depending on the distance.

In a further embodiment, if multiple surgical planning objects are available (e.g. multiple planned craniotomies, screws or trajectories), the augmented visualization of relevant objects may vary as the viewing direction towards the patient changes. E.g. for a surgical spine case with multiple planned screws, not all planned screws are visualized simultaneously as overlays on the patient anatomy. Only the screw best (most orthogonally or most parallel), aligned with the current viewing direction is displayed. Another example could be planned trajectories for leads. Only the lead best (most orthogonally or most parallel) aligned with the viewing direction of the head mounted display is displayed together with the anatomically segmented objects relevant for the respective lead.

In a further embodiment, measurements are displayed in the head mounted display. Depending on the viewing direction of the head mounted display, only the measurements that are almost perpendicular to the viewing direction are displayed. This enables clear visualization of measurements, e.g. in screw planning.

In a further embodiment, in a radiotherapy patient positioning use case, the augmented reality device displays 2D x-ray images perpendicularly aligned to the actual x-ray path of the radiotherapy positioning system. The x-ray images are visible dependent on the angle of the view direction in comparison to the virtual position of the x-ray image. Further, after aligning the augmented reality device view direction with the actual 2D x-ray path, a DRR rendering of the patient's CT images may be displayed overlaid over and registered to the patient's anatomy. This allows a comparison of the 2D x-ray image with the 3D DRR image and thereby enables a correction of the patient positioning. This correction could also be performed with the augmented reality device, e.g. by detecting gestures moving the virtual 3D DRR image to match better with the 2D x-ray images.

In a further embodiment, the augmented reality device has a shutter mechanism that allows the device to control the amount of light entering the device. Thus, the augmented reality device can either display the physical surroundings of the user or completely darken them out. This shutter mechanism is controlled by the view direction. In e.g. a microscope surgery treatment the shutters can be closed when looking at the surgical site, thus looking at the virtual microscope image. When viewing in another direction, e.g. to receive a surgical instrument given to the user by a nurse, the shutter mechanism opens and allows the user to see the physical surroundings.

In a further embodiment, additional information on the surgical or medical procedure is taken into consideration for the visualization. Additional information could be information on the procedure being performed, standardized workflow steps relevant for the current procedure, patient vital signs data and standardized best-practice information on anatomical areas to be treated. E.g. resectability maps that show the ideal area of resection could be shown inside the head mounted display if a workflow step has been reached that requires tumor resection.

In a further embodiment, the head mounted display shows visual information on next workflow steps, e.g. by highlighting patient anatomy or surgical instruments in combination with text description. The visualization is dependent on both current workflow step and the viewing direction of the head mounted display. E.g. surgical instruments are only highlighted if the user looks in the direction of the instruments.

In a further embodiment, the user of a head mounted display may look at an arbitrary device within the OR, for example for a predefined amount of time, whereupon the AR-device projects data into the field of view of the user, which explains the technical properties of the device the user is looking at, for example the measurement readings the device is recording or displaying.

A further aspect of the present invention relates to the use of an AR-device, particularly of AR-goggles or AR-spectacles, for providing an AR-overlay in a medical environment, which is projected into the field of view provided by the AR-device as a function of predefined viewing-characteristics. More specifically, the use of the AR-device may involve performing the method a described above.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect.

A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program.

In a third aspect, the invention is directed to a non-transitory computer-readable program storage medium on which the program according to the second aspect is stored.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the computer-readable program storage medium according to the third aspect.

In a fifth aspect, the invention is directed to a medical system, comprising:
 a) the at least one computer according to the fourth aspect;
 b) at least one electronic data storage device storing at least the patient data; and
 c) an AR-device for providing an AR-overlay,
   wherein the at least one computer is operably coupled to
   the at least one electronic data storage device for acquiring, from the at least one data storage device, at least the patient data, and
   the AR-device for providing an AR-overlay on the basis of the visualization data.

For example, the invention does not involve or in particular comprise or encompass an invasive step which would represent a substantial physical interference with the body requiring professional medical expertise to be carried out and entailing a substantial health risk even when carried out with the required professional care and expertise.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Image registration is the process of transforming different sets of data into one co-ordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

A marker holder is understood to mean an attaching device for an individual marker which serves to attach the marker to an instrument, a part of the body and/or a holding element of a reference star, wherein it can be attached such that it is stationary and advantageously such that it can be detached. A marker holder can for example be rod-shaped and/or cylindrical. A fastening device (such as for instance a latching mechanism) for the marker device can be provided at the end of the marker holder facing the marker and assists in placing the marker device on the marker holder in a force fit and/or positive fit.

A pointer is a rod which comprises one or more—advantageously, two—markers

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

The invention also relates to a navigation system for computer-assisted surgery, comprising:
- a computer for processing the absolute point data and the relative point data;
- a detection device for detecting the position of the main and auxiliary points in order to generate the absolute point data and to supply the absolute point data to the computer;
- a data interface for receiving the relative point data and for supplying the relative point data to the computer; and
- a user interface for receiving data from the computer in order to provide information to the user, wherein the received data are generated by the computer on the basis of the results of the processing performed by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (for example on the surface of) a characteristic anatomical structure of the body part can also represent said structure. The landmark can represent the anatomical Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

For example, the atlas data includes information of the anatomical body part. This information is for example at least one of patient-specific, non-patient-specific, indication-specific or non-indication-specific. The atlas data therefore describes for example at least one of a patient-specific, non-patient-specific, indication-specific or non-indication-specific atlas. For example, the atlas data includes movement information indicating a degree of freedom of movement of the anatomical body part with respect to a given reference (e.g. another anatomical body part). For example, the atlas is a multimodal atlas which defines atlas information for a plurality of (i.e. at least two) imaging modalities and contains a mapping between the atlas information in different imaging modalities (for example, a mapping between all of the modalities) so that the atlas can be used for transforming medical image information from its image depiction in a first imaging modality into its image depiction in a second imaging modality which is different from the first imaging modality or to compare (for example, match or register) images of different imaging modality with one another.

A medical workflow comprises a plurality of workflow steps performed during a medical treatment and/or a medical diagnosis. The workflow steps are typically, but not necessarily performed in a predetermined order. Each workflow step for example means a particular task, which might be a single action or a set of actions. Examples of workflow steps are capturing a medical image, positioning a patient, attaching a marker, performing a resection, moving a joint, placing an implant and the like.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
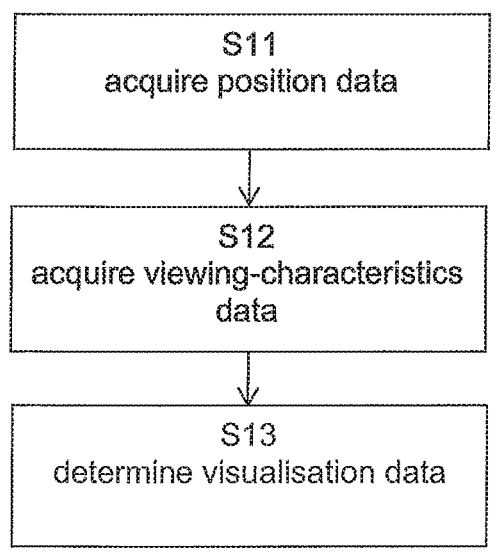
FIG. 1 illustrates the basic method steps according to the present invention.

FIG. 1 illustrates the basic steps of the method according to the first aspect of the present invention, in which step S11 encompasses acquiring position data which describes the relative spatial position of an object with respect to the AR-device and/or the relative spatial position of the object with respect to the user's eyes, step S12 encompasses determining viewing-characteristics data which describe at least one characteristic of the user's view at the object, and the final step S13 encompasses determining visualization data describing the AR-overlay which is projected into the field of view provided by the AR-device.

Figure 2:
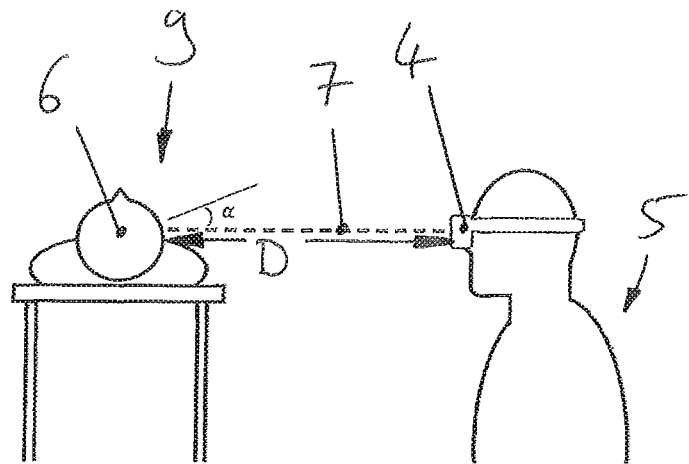
FIGS. 2 and 3 show the use of an AR-device in accordance with the present invention.

FIG. 2 illustrates the use of AR-goggles 4 in a medical environment. Surgeon 5 is wearing AR-goggles 4 which project an AR-overlay into the surgeon 5 field of view. In the shown example, the content of the AR-overlay is dependent on the direction of the visual axis 7 of the AR-goggles 4 with respect to the head 6 of patient 9. The deviating vertical component of the direction of the visual axis 7 is indicated by deviation angle α between the predefined spatial direction and the direction of the visual axis 7). Further, the content of the AR-overlay is also dependent on the distance D between the AR-goggles 4 and the head 6 of patient 9. As soon as surgeon 5 approaches the head 6, thereby decreasing distance D, the AR-overlay may change insofar as smaller structures of an artificial 3D-image-dataset are now projected into the surgeon field of view and therefore become visible for the surgeon 5. As soon as surgeon 5 increases the distance D again, the projection of these smaller structures will end such that surgeon 5 merely sees larger structures within the artificial image-dataset. In a similar manner, different structures contained in the artificial image-dataset may become visible for the surgeon 5, depending on the value of deviation angle α.

Figure 3:
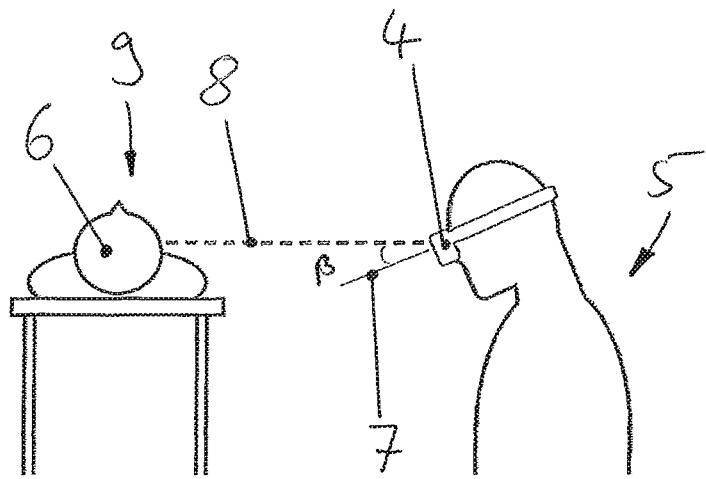

FIG. 3 shows an example in which the content of the AR-overlay depends on whether the surgeon 5 rotates his head downwards, so that the visual axis 7 of the AR-goggles 4 deviates from the connecting line 8 between the AR-goggles 4 and the patient's head 6. In this case the actual viewing direction of surgeon's eyes 5 may still conform to connecting line 8 as the surgeon 5 still looks at the patient's head 6. For example, surgeon 5 may obtain written data within the AR-overlay by merely rotating the head downwards while still looking at the head 6.

Figure 4:
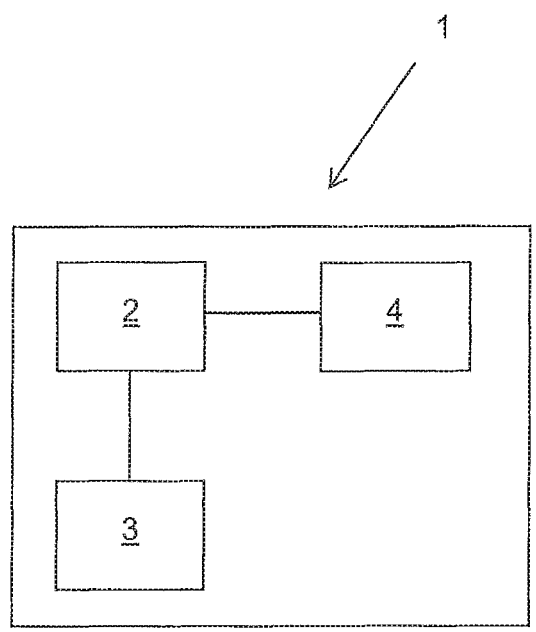
FIG. 4 is a schematic illustration of system according to the present invention.

FIG. 4 is a schematic illustration of the medical system 1 according to the fifth aspect. The system is in its entirety identified by reference sign 1 and comprises a computer 2, an electronic data storage device (such as a hard disc) 3 for storing at least the patient data and AR-device 4 (such as AR-goggles). The components of the medical system 1 have the functionalities and properties explained above with regard to the fifth aspect of this disclosure.

The invention claimed is:

1. A computer-implemented method of providing an AR-overlay in a medical environment, which is projected into a field of view provided by an AR-device particularly by AR-goggles, as a function of predefined viewing-characteristics, the method comprising:
    position data is acquired, describing a spatial position of an object observed through the AR-device relative to the spatial position of the AR-device and/or a spatial position of the eyes of a user of the AR-device;
    viewing-characteristics data is determined based on the position data, describing at least one characteristic of an user's view at the object;
    visualization data is determined based on the viewing-characteristics data, describing the AR-overlay which is projected into the field of view provided by the AR-device, wherein the content of the AR-overlay which is positionally registered with the field-of-view provided by the AR-device is changed in correspondence with a change of at least one characteristic of the user's view;
wherein
    a visualization of larger structures changes to a visualization of smaller structures, specifically in accordance with a decreasing distance between the AR-device and the object, and vice versa;
    different components or parts of a patient's anatomy are displayed, specifically depending on a spatial direction of a visual axis;
    information on the patient's anatomy is displayed, specifically depending on a tilt angle of the AR-device; and/or
    acquired 2D and/or 3D images, measurements, planned craniotomies, trajectories or orientations of instruments or implants are displayed, specifically depending on their alignment with respect to the spatial direction of a visual axis.

2. The method according to claim 1, wherein the viewing-characteristics data describes the following characteristic of the user's view with respect to the object:
    a spatial direction of a visual axis of the AR-device or of a visual axis of the eyes towards the object, particularly a horizontal component and/or a vertical component of the spatial direction.

3. The method according to claim 1, wherein the viewing-characteristics data describes at least one of the following characteristics of the user's view with respect to the object:
    a first deviation angle between a visual axis of the AR-device and a line connecting the object and the AR-device; and
    a second deviation angle between a visual axis of the eyes and a line connecting the object and the eyes;
particularly wherein the viewing-characteristics data describes a horizontal component or a vertical component of the first or second deviation angle.

4. The method according to claim 1, wherein the viewing-characteristics data describes at least one of the following characteristics of the user's view with respect to the object:
    a tilt angle of the AR-device around the visual axis of the AR-device, particularly with respect to a gravitational direction; and
    the distance of the AR-device with respect to the object, particularly along the visual axis of the AR-device.

5. The method according to claim 1, wherein determining visualization data involves changing the AR-overlay in correspondence with a change of at least one characteristics of the user's view.

6. The method according to claim 1, wherein the object observed through the AR-device is one of:
   an anatomical structure, particularly a pathological structure of a patient;
   a medical device, a medical apparatus, a medical instrument or a medical implant; and
   particularly wherein a plurality of objects is observed.

7. The method according to claim 1, wherein the AR-overlay comprises at least one of:
   anatomical visualizations including images and/or virtual images of anatomical structures of a patient, which are in particular segmented;
   anatomical information;
   surgery parameters;
   surgery instructions;
   information on a medical/surgical procedure, particularly on a current and/or subsequent step of the procedure; and
   measurements on the patient's anatomy and/or medical implants;
   particularly wherein the content of the AR-overlay is positionally registered with the field-of-view provided by the AR-device.

8. The method according to claim 1, wherein the AR-device comprises one or more of the following sensors:
   at least one video sensor oriented in a forward direction and substantially aiming to the field-of-view provided by the AR-device;
   at least one video sensor oriented in a backward direction and substantially aiming to at least one eye of the user;
   at least one sensor adapted to sense the spatial position of the AR-device;
   at least one sensor adapted to sense an acceleration of the AR-device; and
   at least one sensor adapted to sense the distance between the AR-device and an object, particularly along the visual axis of the AR-device.

9. The method according to claim 1, wherein the field-of-view provided by the AR-device is darkened out except for a defined region of interest.

10. The method according to claim 1 further comprising providing AR-goggles, for providing an AR-overlay in a medical environment, which is projected into the field of view provided by the AR goggles as a function of predefined viewing-characteristics.

11. A computer-implemented method of providing an AR-overlay in a medical environment, which is projected into a field of view provided by an AR-device particularly by AR-goggles, as a function of predefined viewing-characteristics, the method comprising:
   position data is acquired, describing a spatial position of an object observed through the AR-device relative to the spatial position of the AR-device and/or the spatial position of the eyes of a user of the AR-device;
   viewing-characteristics data is determined based on the position data, describing at least one characteristic of an user's view at the object;
   visualization data is determined based on the viewing-characteristics data, describing the AR-overlay which is projected into the field of view provided by the AR-device, wherein the content of the AR-overlay which is positionally registered with the field-of-view provided by the AR-device is changed in correspondence with a change of at least one characteristic of the user's view; and
   wherein acquiring position data involves acquiring acceleration data describing a magnitude of an acceleration of the AR-device, and wherein the visualization data is also determined based on the magnitude of the acceleration.

12. A computer-implemented method of providing an AR-overlay in a medical environment, which is projected into a field of view provided by an AR-device particularly by AR-goggles, as a function of predefined viewing-characteristics, the method comprising:
   position data is acquired, describing a spatial position of an object observed through the AR-device relative to the spatial position of the AR-device and/or the spatial position of the eyes of a user of the AR-device;
   viewing-characteristics data is determined based on the position data, describing at least one characteristic of an user's view at the object;
   visualization data is determined based on the viewing-characteristics data, describing the AR-overlay which is projected into the field of view provided by the AR-device, wherein the content of the AR-overlay which is positionally registered with the field-of-view provided by the AR-device is changed in correspondence with a change of at least one characteristic of the user's view; and
   wherein at least one X-ray-image is displayed, which is registered with a patient's anatomy within the field-of-view provided by the AR-device, and wherein, when a spatial direction of a visual axis of the AR-device or the eyes substantially corresponds to the direction of an X-ray-path, at least one CT-image, particularly a DDR-rendering thereof is displayed, which is registered with the patient's anatomy within the field-of-view provided by the AR-device.

13. A non-transitory computer readable medium comprising instructions which when executed by at least one processor, execute the steps of:
   position data is acquired, describing a spatial position of an object observed through an AR-device relative to the spatial position of the AR-device and/or the spatial position of the eyes of a user of the AR-device;
   viewing-characteristics data is determined based on the position data, describing at least one characteristic of an user's view at the object;
   visualization data is determined based on the viewing-characteristics data, describing the AR-overlay which is projected into a field of view provided by the AR-device, wherein the content of the AR-overlay which is positionally registered with the field-of-view provided by the AR-device is changed in correspondence with a change of at least one characteristic of the user's view; wherein
   a visualization of larger structures changes to a visualization of smaller structures, specifically in accordance with a decreasing distance between the AR-device and the object, and vice versa;
   different components or parts of a patient's anatomy are displayed, specifically depending on a spatial direction of a visual axis;
   information on the patient's anatomy is displayed, specifically depending on a tilt angle of the AR-device; and/or
   acquired 2D and/or 3D images, measurements, planned craniotomies, trajectories or orientations of instruments or implants are displayed, specifically depending on their alignment with respect to the spatial direction of a visual axis.

14. A medical system, comprising:

at least one computer having at least one processor and memory, the memory having instructions stored thereon to cause the at least one processor to:

position data is acquired, describing a spatial position of an object observed through an AR-device relative to the spatial position of the AR-device and/or the spatial position of the eyes of a user of the AR-device;

viewing-characteristics data is determined based on the position data, describing at least one characteristic of an user's view at the object; and visualization data is determined based on the viewing-characteristics data, describing the AR-overlay which is projected into a field of view provided by the AR-device, wherein the content of the AR-overlay which is positionally registered with the field-of-view provided by the AR-device is changed in correspondence with a change of at least one characteristic of the user's view;

wherein a visualization of larger structures changes to a visualization of smaller structures, specifically in accordance with a decreasing distance between the AR-device and the object, and vice versa;

different components or parts of a patient's anatomy are displayed, specifically depending on a spatial direction of a visual axis;

information on the patient's anatomy is displayed, specifically depending on a tilt angle of the AR-device; and/or acquired 2D and/or 3D images, measurements, planned craniotomies, trajectories or orientations of instruments or implants are displayed, specifically depending on their alignment with respect to the spatial direction of a visual axis;

at least one electronic data storage device storing at least a patient data; and an AR-device for providing an AR-overlay, wherein the at least one computer is operably coupled to the at least one electronic data storage device for acquiring, from the at least one data storage device, at least the vizualization data, and the AR-device for providing an AR-overlay on the basis of the visualization data.

* * * * *